United States Patent [19]

Alving et al.

[11] Patent Number: 5,910,306
[45] Date of Patent: Jun. 8, 1999

[54] TRANSDERMAL DELIVERY SYSTEM FOR ANTIGEN

[75] Inventors: Carl R. Alving; Gregory M. Glenn, both of Bethesda, Md.

[73] Assignee: The United States of America as represented by the Secretary of the Army, Washington, D.C.

[21] Appl. No.: 08/749,164

[22] Filed: Nov. 14, 1996

[51] Int. Cl.[6] ........................ A61K 39/00; A61K 39/002; A61K 39/02; A61K 39/12
[52] U.S. Cl. ........................ 424/184.1; 424/449; 424/450; 424/204.1; 424/234.1; 424/265.1; 424/269.1; 424/274.1; 424/277.1; 424/279.1; 424/282.1; 424/283.1; 424/810; 424/812
[58] Field of Search ........................ 424/444, 450, 424/234.1, 282.1, 810, 812, 184.1, 204.1, 265.1, 269.1, 274.1, 277.1, 283.1, 279.1, 449, 573; 514/2; 435/6, 7.24

[56] References Cited

U.S. PATENT DOCUMENTS

| | | |
|---|---|---|
| 4,196,191 | 4/1980 | Almeida . |
| 4,455,142 | 6/1984 | Martins . |
| 4,484,923 | 11/1984 | Amkraut . |
| 4,876,278 | 10/1989 | Taylor . |
| 4,877,612 | 10/1989 | Berger . |
| 4,921,757 | 5/1990 | Wheatley . |
| 4,929,442 | 5/1990 | Powell . |
| 5,008,050 | 4/1991 | Cullis . |
| 5,059,421 | 10/1991 | Loughrey . |
| 5,169,637 | 12/1992 | Lenk . |
| 5,200,393 | 4/1993 | Weiner . |
| 5,256,422 | 10/1993 | Albert . |
| 5,260,066 | 11/1993 | Wood . |
| 5,326,790 | 7/1994 | Thornfeldt . |
| 5,332,576 | 7/1994 | Mantelle . |
| 5,340,588 | 8/1994 | Domb . |
| 5,352,449 | 10/1994 | Beltz . |
| 5,464,386 | 11/1995 | Hofmann . |
| 5,601,827 | 2/1997 | Collier . |
| 5,607,691 | 3/1997 | Hale . |
| 5,733,572 | 3/1998 | Unger ........................ 424/450 |

FOREIGN PATENT DOCUMENTS

| | | |
|---|---|---|
| 47099/89 | 6/1990 | Australia . |
| 92/03122 | 3/1992 | WIPO . |

OTHER PUBLICATIONS

Hsiung, GD and Fong, CKY, Diagnostic Virology, 3rd ed., Yale Univ. Press, New Haven, CT, pp. 29–34, 1982.
Lane, HC, Whalen G, and Fauci AS, In vitro evaluation of human lymphocyte function, In: Cellular Immunology, DM Weir, ed., Blackwell Scientific Pub. Boston, MA, pp. 66.5–66.7, 1986.
Becker, *Experimental Dermatology*, 2:63–69, 1993.
Blauvelt, *Journal of Investigative Dermatology*, 104:293–296, 1995.
Bowen, *Immunology*, 81:338–342, 1994.
Chin, *Veterinary Microbiology*, 43:21–32, 1995.
Chin, *Journal of Biotechnology*, 44:13–19, 1996.
Condon, *Nature Medicine*, 2:1122–1128, 1996.
Enk, *Journal of Immunology*, 151:2390–2398, 1993.
Goodnow, *Immunological Reviews*, 156:5–10, 1997.
Knop, *International Archives of Allergy and Immunology*, 107:231–232, 1995.
Mahmoud, *Science*, 246:1015–1022, 1989.
Peters, *Immunology Today*, 17:273–278, 1996.
Schwarzenberger, *Journal of Investigative Dermatology*, 106:553–558, 1996.
Stacey, *Journal of Immunology*, 157:2116–2122, 1996.
Steinman, *Immunological Review*, 156:25–37, 1997.
Stingl, *Immunological Series*, 46:3–72, 1989.
Udey, *Clinical and Experimental Immunology*, 107(suppl. 1):6–8, 1997.
Alving, *Vaccine* 4:166–172, 1986.
Alving, *Journal of Immunological Methods*, 140:1–13, 1991.
Alving, *Immunobiol.*, 187:430–446, 1993.
Alving, *NY Acad. Sci.*, 690:265–275, 1993.
Alving, *AIDS Research and Human Retroviruses*, 10:S91–S94, 1994.
Alving, *Immunological Reviews*, No. 145, 5–31, 1995.
Egbaria, *Advanced Drug Delivery Reviews*, 5:287–300, 1990.
Fleisher, *Life Sciences*, 57:1293–1297, 1995.
Glenn, *Immunology Letters*, 47:73–78, 1995.
Gupta, *Vaccine*, 13:1263–1276, 1995.
de Haan, *Vaccine*, 13:1320–1324, 1995.
Korting, *Journal of the American Academy of Dermatology*, 25:1068–1071, 1991.
Korting, *British Journal of Dermatology*, 132:571–579, 1995.
Mengiardi, *Vaccine*, 13:1306–1315, 1995.
Mezei, *Life Sciences*, 26:1473–1477, 1980.
Moghimi, *J. Microencapsulation*, 10:155–162, 1993.
Norimatsu, *Vaccine*, 13:1325–1329, 1995.
Paul, *Vaccine Research*, 4:145–164, 1995.
Paul, *Eur. J. Immunol.*, 25:3521–3524, 1995.
Powers, *Vaccine*, 13:1330–1335, 1995.
Ranade, *J. Clin. Pharmacol.*, 31:401–418, 1991.
Rao, *Infection and Immunity*, 63:2396–2402, 1995.
Sauzet, *Vaccine*, 13:1339–1345, 1995.
Schäfer–Korting, *Journal of the American Academy of Dermatology*, 21:1271–1275, 1989.
Verma, *Biochimica et Biophysica Acta*, 1066:229–238, 1991.

(List continued on next page.)

*Primary Examiner*—David Saunders
*Assistant Examiner*—Mary Beth Tung
*Attorney, Agent, or Firm*—Pillsbury Madison & Sutro LLP

[57] ABSTRACT

A transdermal liposome system delivers antigen to immune cells without perforation of the skin, and induces an immune response in an animal or human. The system uses liposomes to deliver a variety of antigens which can elicit an antigen-specific immune response (e.g., humoral and/or cellular effectors) after topical application of a formulation containing liposomes and antigen to intact skin of the animal or human.

29 Claims, No Drawings

OTHER PUBLICATIONS

Verma, *Infection and Immunity*, 60:2438–2444, 1992.
Vutla, *Journal of Pharmaceutical Sciences*, 85:5–8, 1996.
Wang, *The Journal of Immunology*, 156:4079–4082, 1996.
Wang, *The Journal of Immunology*, 154:2784–2793, 1995.
Wassef, *Immunomethods*, 4:217–222, 1994.
Weiner, *Antimicrobial Agents and Chemotherapy*, 33:1217–1221, 1989.
White, *Vaccine*, 11:1341–1346, 1993.
White, *Vaccine*, 13:1111–1122, 1995.
Yasutomi, *Journal of Virology*, 69:2279–2284, 1995.
Zellmer, *Biochimica et Biophysica Acta*, 1237:176–182, 1995.
Alving, In: *Liposome Technology*, 2nd Ed. (Gregoriadis, ed.), CRC Press, pp. 317–343, 1993.
Small, In: *Handbook of Lipid Research*, Plenum, 4:43–87.
Small, In: *Handbook of Lipid Research*, Plenum, 4:89–96.

TRANSDERMAL DELIVERY SYSTEM FOR ANTIGEN

BACKGROUND

1. Field of the Invention

The invention relates to transdermal delivery of antigen by a liposome formulation to induce an antigen-specific immune response.

2. Description of the Related Art

Liposomes are smectic mesophases, which have been defined in the following manner by D. M. Small (Handbook of Lipid Research, Vol. 4, Plenum, N.Y., pp. 49–50): "When a given molecule is heated instead of melting directly into anisotropic lipid it may instead pass through intermediate states called mesophases or liquid crystals, characterized by residual order in some directions but by lack of order in others . . . In general, the molecules of liquid crystals are somewhat longer than they are wide and have a polar or aromatic part somewhere along the length of the molecule. The molecular shape and the polar-polar or aromatic interaction permit the molecules to align in a partial ordered array . . . These structures characteristically occur in molecules that possess a polar group at one end. Liquid crystals with long range order in the direction of the long axis of the molecule are called smectic, layered, or lamellar liquid crystals . . . in the smectic states, the molecules may be in single or double layers, normal or tilted to the plane of the layer, and with frozen or melted aliphatic chains."

As an example of work in the field of transdermal delivery of antigen, Paul et al. (1995) and Paul and Cevc (1995) (hereinafter "the Cevc lab") were not able to use liposomes for transdermal immunization. The Cevc lab used three different lipid formulations: mixed micelles, liposomes, and transfersomes in attempting to cause the transdermal delivery of antigen. Lipid was provided as an ethanol solution of soybean phosphatidylcholine (SPC); liposomes were formed by sonication, then freeze-thawed, and finally filtered for the purposes of sterilization and improved sample homogeneity. Mixed micelles contained SPC and bile salt (BS) in a mole ratio of 1:1, transferosomes contained SPC and BS in a mole ratio of 9:2, and liposomes contained SPC but no BS.

Because they contain a significant proportion of bile salts, mixed micelles and transferosomes cannot be considered liposomes (i.e., smectic mesophases) as stated by D. M. Small (Handbook of Lipid Research, Vol. 4, Plenum, N.Y., p. 95): "Class IIIA lipids . . . exhibit lyotropic mesomorphism at low water concentrations and form liquid crystals . . . At higher water concentrations, however, these liquid crystals dissolve to form micelles. Aliphatic molecules such as soaps, lysolecithin, and aliphatic detergents, are representative of class IIA lipids. In class IIIB lipids . . . bulky aromatic ring systems often comprise the hydrophobic component of the molecule. These compounds form micelles, but do not form liquid crystals. Molecules typical of this class are bile salts (e.g., Na cholate, Na deoxycholate, and Na chenodeoxycholate), saponins, and rosin soaps." As noted above in Small's definition of smectic mesophases, liposomes are a type of liquid crystals.

FIG. 1 of Paul et al. (1995) shows that only a formulation of antigen and transferosomes induced an immune response as measured by titer of antigen-specific antibody. Topically applied formulations of antigen in solution, antigen and mixed micelles, and antigen and liposomes (i.e., smectic mesophases) did not induce an immune response equivalent to that induced by subcutaneous injection. Therefore, there was a positive control (i.e., antigen and transfersomes) to validate their negative conclusion that a formulation of antigen and liposomes did not cause transdermal immunization.

Moreover, Paul and Cevc (1995) state on page 145, "Large molecules normally do not get across the intact mammalian skin. It is thus impossible to immunize epicutaneously with simple peptide or protein solutions." They conclude, "The dermally applied liposomal or mixed micellar immunogens are biologically as inactive as simple protein solutions, whether or not they are combined with the immunoadjuvant lipid A."

Despite the aforementioned contrary teaching, we have found that liposomes do provide a transdermal delivery system for antigen that can induce an antigen-specific immune response.

SUMMARY OF THE INVENTION

An objective of the invention is to provide a transdermal delivery system that induces an immune response (e.g., humoral and/or cellular effectors) in an animal or human. Such a system provides a simple means to present antigen to the immune system of the animal or human.

In addition to eliciting immune reactions leading to generation of an antigen-specific B lymphocyte and/or T lymphocyte, including a cytotoxic T lymphocyte (CTL), another objective of the invention is to positively and/or negatively regulate components of the immune system by using the transdermal delivery system to affect antigen-specific helper (Th1 and/or Th2) or delayed-type hypersensitivity ($T_{DTH}$) T-cell subsets.

In one embodiment of the invention, a formulation containing liposomes and antigen is applied to intact skin of an organism, the antigen is presented to immune cells, and an antigen-specific immune response is induced without perforating the skin. The formulation may include additional antigens such that topical application of the formulation induces an immune response to multiple antigens. In such a case, the antigens may or may not be derived from the same source, but the antigens will have different chemical structures so as to induce immune responses specific for the different antigens. Antigen-specific lymphocytes may participate in the immune response and, in the case of participation by B lymphocytes, antigen-specific antibodies may be part of the immune response.

In a second embodiment of the invention, the above method is used to treat an organism. If the antigen is derived from a pathogen, the treatment vaccinates the organism against infection by the pathogen. A formulation that includes a tumor antigen may provide a cancer treatment; a formulation that includes an autoantigen may provide a treatment for a disease caused by the organism's own immune system (e.g., autoimmune disease).

In a third embodiment of the invention, a patch for use in the above methods is provided. The patch comprises a dressing, liposomes, and a therapeutically effective amount of antigen. The dressing may be occlusive or non-occlusive. The patch may include additional antigens such that application of the patch induces an immune response to multiple antigens. In such a case, the antigens may or may not be derived from the same source, but the antigens will have different chemical structures so as to induce an immune response specific for the different antigens.

Moreover, in a fourth embodiment of the invention, the formulation is applied to intact skin overlying more than one draining lymph node field using either single or multiple applications. The formulation may include additional antigens such that application to intact skin induces an immune response to multiple antigens. In such a case, the antigens may or may not be derived from the same source, but the antigens will have different chemical structures so as to induce an immune response specific for the different antigens.

The antigen may be derived from a pathogen that can infect the organism (e.g., bacterium, virus, fungus, Rickettsia, or parasite), or a cell (e.g., tumor cell or normal cell). The antigen may be a tumor antigen or an autoantigen. Chemically, the antigen may be a carbohydrate, glycolipid, glycoprotein, lipid, lipoprotein, peptide, phospholipid, or protein. Protein may be obtained by recombinant means, chemical synthesis, or purification from a natural source. The molecular weight of the antigen may be greater than 500 daltons, preferably greater than 800 daltons, and more preferably greater than 1000 daltons.

Liposomes may be multilamellar, paucilamellar, or unilamellar; the liposomes may be phospholipid liposomes containing phospholipid, sterol, or a mixture thereof. The phospholipid may be phosphatidylcholine, phosphatidylglycerol, diphosphatidylglycerol, phosphatidylserine, phosphatidylinositol, phosphatidic acid, lysophosphatide, sphingomyelin, or mixtures thereof. The sterol is a derivative based on the cyclopentanophenanthrene nucleus, and is preferably cholesterol, cholesterol esters, cholesterol sulphates, or mixtures thereof. A liposome may also contain a nonphospholipid such as, for example, ceramide, cerebroside, glycosphingolipid, sphingolipid, free fatty acids, eicosanoids, and lipid vitamins. Liposomes may contain a nonionic amphiphile such as, for example, polyoxyethylene fatty acid ester, polyoxyethylene fatty acid ether, diethanolamide, long chain acyl hexosamide, long chain acyl amino acid amide, long chain amino acid amine, polyoxyethylene sorbitan ester, polyoxyethylene glyceryl ester, polyoxyethylene glyceryl diester, glycerol stearate, glycerol distearate, glycerol oleate, glycerol dioleate, glycerol palmitate, glycerol dipalmitate, or mixtures thereof. Liposomes may contain an ionic amphiphile such as, for example, betaine, sarcosinate, monomeric alkyd, dimeric alkyd, dimethyl distearyl amine, or mixtures thereof.

The formulation may further comprise an adjuvant. Inclusion of an adjuvant may allow potentiation or modulation of the immune response. Moreover, selection of a suitable antigen or adjuvant may allow preferential induction of a humoral or cellular immune response, specific antibody isotypes (e.g., IgM, IgD, IgA1, IgA2, IgE, IgG1, IgG2, IgG3, and/or IgG4), and/or specific T-cell subsets (e.g., CTL, Th1, Th2 and/or $T_{DTH}$).

The term "antigen" as used in the invention, is meant to describe a substance that induces a specific immune response when presented to immune cells of an organism. An antigen may comprise a single immunogenic epitope, or a multiplicity of immunogenic epitopes recognized by a B-cell receptor (i.e., antibody on the membrane of the B cell) or a T-cell receptor.

The term "therapeutically effective amount" as used in the invention, is meant to describe that amount of antigen which induces an antigen-specific immune response. Such induction of an immune response may provide a treatment such as, for example, immunoprotection, immunosuppression, modulation of autoimmune disease, potentiation of cancer immunosurveillance, or vaccination against an infectious disease caused by a pathogen.

DETAILED DESCRIPTION OF THE INVENTION

Liposomes of the invention are closed vesicles surrounding an internal aqueous space. The internal compartment is separated from the external medium by a lipid bilayer composed of discrete lipid molecules. They may be composed of a variety of lipid components such as, for example, phospholipid, nonionic surfactant, synthetic or natural lipid, saturated or unsaturated lipid, and charged or neutral lipid, either with or without a sterol. Liposomes may be either multilamellar, paucilamellar, or unilamellar, and may be made in different sizes: small being less than 25 nm, intermediate being 25 nm to 500 nm, and large being greater than 500 nm. A typical liposome is composed of dimyristoyl phosphatidylcholine (DMPC), dimyristoyl phosphatidylglycerol (DMPG), and cholesterol, with or without lipid A, in a multilamellar configuration, and has a population of sizes from about 0.2 µm to about 10 µm. Antigen is delivered by the delivery system through intact skin to cells of the immune system, where an immune response is induced.

Liposomes of the invention are used as a transdermal delivery system of agents that induce an immune response. These agents as a class can be called antigens. Antigen may be composed of chemicals such as, for example, carbohydrate, glycolipid, glycoprotein, lipid, lipoprotein, peptide, phospholipid, protein or any other material known to induce an immune response. Antigen may be provided as a whole organism such as, for example, a virion; antigen may be obtained from an extract or lysate, either from whole cells or membrane alone; or antigen may be chemically synthesized or produced by recombinant means.

Liposomes may be preformed and then mixed with antigen. Liposomes may also be formed so as to contain antigen inserted in the lipid bilayer, in the inner aqueous spaces, associated with the outer leaflet of the lipid bilayer, in the surrounding solution, or in any combination of these arrangements. The antigen may be dissolved or suspended, and then added to (a) the preformed liposomes in a lyophilized state, (b) dried lipids as a swelling solution or suspension, or (c) the solution of lipids used to form liposomes. The liposomes may either be used unwashed, or washed prior to use to remove antigen that is not associated with the liposome.

The liposomes may contain a single antigen, more than one antigen, or the liposomes containing separate antigens may be mixed into a single liposome formulation. The multivalent antigen formulation may be used to induce an immune response to more than one antigen at the same time.

The liposomes may be applied in the form of an emulsion, gel, solution, suspension, or other forms known in the art.

In addition to the above ingredients, there may also be incorporated other pharmaceutically acceptable additives including, for example, diluents, binders, stabilizers, preservatives, and colorings.

An object of the invention is to provide a novel means for vaccination through intact skin without the need for penetration of the skin. The transdermal delivery system provides a method whereby antigens can be delivered to the immune system, especially specialized immune cells underlying the skin. A mixture of antigen and liposomes; or antigen encapsulated in, attached to, or associated with the lipid bilayer of liposomes may be applied with or without adjuvants.

Without being bound to any particular theory but only to provide an explanation for our observations, it is presumed that the transdermal liposome delivery system carries antigen to cells of the immune system where an immune response is induced. The antigen may pass through the normal protective outer layers of the skin (i.e., stratum corneum) and induce the immune response directly, or through an antigen presenting cell (e.g., macrophage, tissue macrophage, Langerhans cell, dendritic cell, B lymphocyte, or Kupffer cell) that presents processed antigen to a T lymphocyte. Passage of liposomes through the stratum corneum may not be necessary to deliver antigen to cells of the immune system.

LIPOSOME LIPID

Liposomes may be prepared using a variety of techniques and membrane lipids (reviewed in Gregoriadis, 1993).

Natural sources may provide liposome lipid such as, for example, lecithin (i.e., phosphatidylcholine): egg yolk, soybean, and brain. Synthetic lipids are preferred for their chemical purity. Synthetic lecithins are available with fatty acyl chain lengths ranging from 4 to 19 carbons; preferred chain lengths are those in the biological range (12 to 24 carbons).

Liposomes of the invention may be formed from a phospholipid such as, for example, phosphatidylcholine, phosphatidylglycerol, diphosphatidylglycerol, phosphatidylserine, phosphatidic acid, phosphatidylinositol, lysophosphatide, and sphingomyelin. If a sterol is used to stabilize the lipid bilayer, it is preferably cholesterol, a cholesterol ester, or a cholesterol sulphate. Cholesterol may be recrystallized to avoid the possibility of immunosuppression or toxicity due to oxidation products.

Liposomes of the invention may be formed from lipids extracted from the stratum corneum including, for example, ceramide and cholesterol derivatives (Wertz, 1992).

Liposomes of the invention may contain a nonionic amphiphile as a major structural component (by weight) of the lipid bilayer. The nonionic amphiphile may be, for example, polyoxyethylene fatty acid ester, polyoxyethylene fatty acid ether, diethanolamide, long chain acyl hexosamide, long chain acyl amino acid amide, long chain amino acid amine, polyoxyethylene sorbitan ester, polyoxyethylene glyceryl ester, polyoxyethylene glyceryl diester, glycerol stearate, glycerol distearate, glycerol oleate, glycerol dioleate, glycerol palmitate, glycerol dipalmitate, or mixtures thereof. Nonionic amphiphiles that form liposomes in the presence of steroid are disclosed in U.S. Pat. No. 4,917,951, incorporated herein by reference. The lipid bilayer may contain an ionic amphiphile in lieu of some, or all, of the nonionic amphiphile. The ionic amphiphile may be, for example, betaine, sarcosinate, monomeric alkyd, dimeric alkyd, dimethyl distearyl amine, or mixtures thereof. Ionic amphiphiles are disclosed in U.S. Pat. No. 5,164,191, incorporated herein by reference.

Stability, rigidity, and permeability of the liposome is altered by changes in lipid composition. Membrane fluidity is generally controlled by the fatty acyl chains of the lipid. The fatty acyl chain can exist in an ordered, rigid state or in a relatively disordered fluid state. Factors affecting rigidity include chain length and degree of saturation of the fatty acyl chains and temperature. Longer chains interact more strongly with each other so fluidity is greater with short chains; saturated fatty acyl chains are more flexible than unsaturated fatty acyl chains. Transition of the membrane from the rigid to the fluid state occurs as the temperature is raised above the melting temperature. The melting temperature is dependent on the length and degree of saturation of the fatty acyl chain.

ANTIGEN

Antigen of the invention may be expressed by recombinant means, preferably as a fusion with an affinity or epitope tag (Goeddel, 1990; Kriegler, 1990; Ausubel et al., 1996); chemical synthesis of peptide, either free or conjugated to carrier proteins, may be used to obtain antigen of the invention (Bodanszky, 1993; Wisdom, 1994).

Peptide lengths of 6 residues to 20 residues are preferred. Peptides may also by synthesized as branched structures such as those disclosed in U.S. Pat. Nos. 5,229,490 and 5,390,111, incorporated herein by reference. Antigenic peptides include, for example, synthetic or recombinant B-cell and T-cell epitopes, universal T-cell epitopes, and mixed T-cell epitopes from one organism or disease and B-cell epitopes from another.

Antigen obtained through recombinant means or peptide synthesis, as well as antigen of the invention obtained from natural sources or extracts, may be purified by means of the antigen's physical and chemical characteristics, preferably by fractionation or chromatography (Janson and Ryden, 1989; Deutscher, 1990; Scopes, 1993).

Antigen includes, for example, toxins, toxoids, and/or subunits thereof (e.g., cholera toxin, tetanus toxoid).

Antigen is solubilized prior to mixing with liposomes. Suitable buffers include, but are not limited to, phosphate buffered saline $Ca^{++}/Mg^{++}$ free (PBS), normal saline, and TRIS buffer. Antigen not soluble in neutral buffer can be solubilized in 10 mM acetic acid and then diluted to the desired volume with a neutral buffer such as PBS. In the case of one antigen soluble only at acid pH, acetate-PBS at acid pH was used as a diluent after solubilization in 10 mM acetic acid.

Antigen can also be solubilized in a detergent (e.g., a cell membrane extract) along with the lipids themselves, and liposomes are then formed by removal of the detergent by dilution, dialysis, or column chromatography. Certain antigens such as, for example, those from a virus (e.g., hepatitis A) need not be soluble per se, but can be incorporated directly into a liposome in the form of a virosome.

Plotkin and Mortimer (1994) provide antigens which can be used to vaccinate animals or humans to induce an immune response specific for particular pathogens, as well as methods of preparing antigen, determining a suitable dose of antigen, assaying for induction of an immune response, and treating infection by a pathogen (e.g., bacterium, virus, fungus, Rickettsia, or parasite).

Bacteria include, for example: anthrax, campylobacter, cholera, diptheria, enterotoxigenic *E. coli*, giardia, gonococcus, *Hemophilus influenza* B, *Hemophilus influenza* non-typable, meningococcus, pertussis, pneumococcus, salmonella, shigella, tetanus, and yersinia. Viruses include, for example: adenovirus, dengue serotypes 1 to 4 (Delenda et al., 1994; Fonseca et al., 1994; Smucny et al., 1995), ebola (Jahrling et al., 1996), enterovirus, hepatitis serotypes A to E (Blum, 1995; Katkov, 1996; Lieberman and Greenberg, 1996; Mast, 1996; Shafara et al., 1995; Smedila et al., 1994; U.S. Pat. Nos. 5,314,808 and 5,436,126), herpes simplex virus 1 or 2, human immunodeficiency virus (Deprez et al., 1996), influenza, Norwalk, papilloma virus, parvovirus B19, rabies, rotavirus, rubella, rubeola, varicella, and yellow fever. Parasites include, for example: Plasmodium (Bathurst et al., 1993; Chang et al., 1989, 1992, 1994; Fries et al., 1992a, 1992b; Herrington et al., 1991; Khusmith et al., 1991; Malik et al., 1991; Migliorini et al., 1993; Pessi et al., 1991; Tam, 1988; Vreden et al., 1991; White et al., 1993; Wiesmueller et al., 1991) and Leishmania (Frankenburg et al., 1996).

ADJUVANT

The formulation of liposomes and antigen may also contain an adjuvant. Adjuvants are substances that are used to specifically or nonspecifically potentiate an antigen-specific immune response. Usually, the adjuvant and the formulation are mixed prior to presentation of the antigen but, alternatively, they may be separately presented within a short interval of time. Suitable adjuvants include, for example, an oil emulsion (e.g., complete or incomplete Freund's adjuvant), a chemokine (e.g., defensins 1 or 2, RANTES, interleukin-8) or a cytokine (e.g., interleukin-1, -2, -6, or -12; γ-interferon; tumor necrosis factor; or granulocyte-monocyte-colony stimulating factor) (reviewed in Nohria and Rubin, 1994), a muramyl dipeptide derivative (e.g., murabutide, threonyl-MDP or muramyl tripeptide), a heat shock protein or a derivative, a derivative of *Leishmania major* LeIF (Skeiky et al., 1995), cholera toxin or cholera toxin B, or a lipopolysaccharide (LPS) derivative (e.g., lipid A or monophosphoryl lipid A). An adjuvant may be chosen to preferentially induce antibody or cellular effectors, specific antibody isotypes (e.g., IgM, IgD, IgA1, IgA2, secretory IgA, IgE, IgG1, IgG2, IgG3, and/or IgG4), or specific T-cell subsets (e.g., CTL, Th1, Th2 and/or $T_{DTH}$) (Glenn et al., 1995).

Lipid A is derived from the lipopolysaccharide (LPS) of gram-negative bacterial endotoxin. It is an outstanding adjuvant that can be incorporated into the liposome bilayer to induce an immune response to a liposome-associated antigen (Alving, 1993). Lipid A is actually a heterogeneous mixture of compounds having similar structures (Banerji and Alving, 1979). The methods ordinarily used to obtain lipid A can produce a crude fraction, which is then purified by ethylenediamine tetraacetic acid and chloroform extraction to give a purified lipid A that is chloroform soluble (Banerji and Alving, 1979).

PREPARATION OF LIPOSOMES

Chloroform is a preferred solvent for lipids, but it may deteriorate upon storage. Therefore, at one- to three-month intervals, chloroform is redistilled prior to its use as the solvent in forming liposomes. After distillation, 0.7% ethanol can be added as a preservative. Ethanol and methanol are other suitable solvents.

The lipid solution used to form liposomes is placed in a round-bottomed flask. Pear-shaped boiling flasks are preferred, particularly those flasks sold by Lurex Scientific (Vineland, N.J., cat. no. JM-5490). The volume of the flask should be more than ten times greater than the volume of the anticipated aqueous suspension of liposomes to allow for proper agitation during liposome formation.

Using a rotary evaporator, solvent is removed at 37° C. under negative pressure for 10 minutes with a filter aspirator attached to a water faucet. The flask is further dried under low vacuum (i.e., less than 50 μm Hg) for 1 hour in a dessicator.

To encapsulate antigen into liposomes, an aqueous solution containing antigen may be added to lyophilized liposome lipids in a volume that results in a concentration of approximately 200 mM with respect to liposome lipid, and shaken or vortexed until all the dried liposome lipids are wet. The liposome-antigen mixture may then be incubated for 18 hours to 72 hours at 40° C. The liposome-antigen formulation may be used immediately or stored for several years.

It may be advantageous to employ the liposome-antigen mixture directly in the transdermal delivery system. But if removal of non-encapsulated antigen from the mixture is desired, approximately 20 volumes of buffer may be added to the mixture and the liposomes pelleted by centrifugation at 25,000 g to 30,000 g for 30 minutes at 20° C. to 25° C. After removal of the clear (or slightly turbid) supernatant fraction, the liposome pellet may be suspended to the desired final volume (10 mM to 200 mM with respect to liposome lipids) with the appropriate buffer.

Alternatively, liposomes may be formed as described above but without addition of antigen to the aqueous solution. Antigen may then be added to the preformed liposomes and, therefore, antigen would be in solution and/or associated with, but not encapsulated by, the liposomes.

A method for forming liposomes containing at least two lipids or amphiphiles is disclosed in U.S. Pat. No. 5,260,065, incorporated herein by reference.

A method and apparatus for forming liposomes without using a solvent are disclosed in U.S. Pat. Nos. 4,895,452 and 4,911,928, incorporated herein by reference. The lipid phase of the formulation is heated until flowing, and then blended with an excess of the aqueous phase under shear conditions until liposomes are formed. If an oil or a water immiscible component of the formulation (e.g., antigen or adjuvant) is to be encapsulated in the liposome or incorporated in the lipid bilayer, such a component can be blended first with the lipid phase before hydration by the aqueous phase.

Other methods for forming liposomes are disclosed in U.S. Pat. Nos. 4,089,801, 4,196,191, 4,235,871, 4,485,054, 4,508,703, 4,731,210, 4,897,269, 4,963,297, 4,975,282, 5,008,050, 5,059,421, and 5,169,637, incorporated herein by reference. A method for obtaining an oil-in-water emulsion containing liposomes is disclosed in U.S. Pat. No. 3,957,971, incorporated herein by reference; a method for obtaining a water-in-oil emulsion containing liposomes is disclosed in U.S. Pat. No. 5,256,422, incorporated herein by reference. If the process for forming liposomes would denature the antigen in the formulation, the antigen will be mixed with the formed liposomes. Therefore, antigen would not be encapsulated by liposomes formed by such an antigen-denaturing process but, instead, the antigen would only be mixed in solution and/or associated with the liposomes.

Lipid compositions and methods for forming unilamellar liposomes are disclosed in U.S. Pat. Nos. 4,853,228 and 5,008,050, incorporated herein by reference.

Several types of liposomes, such as unilamellar, paucilamellar, or multilamellar vesicles, might be used as a transdermal delivery system for antigens. However, because they are easier to manufacture and require less handling, and consequently afford less chances for contamination, we have used multilamellar vesicles in the Examples below.

TRANSDERMAL DELIVERY OF ANTIGEN

Liposomes have been used as carriers in adjuvants to enhance the immune response to antigens mixed with, encapsulated in, attached to, or associated with liposomes. For previous vaccine applications using liposomes, the formulation was injected through the skin with a needles, as are the majority of licensed vaccines. Injection of vaccines using needles carries certain drawbacks including the need for sterile needles and syringes, trained medical personnel to administer the vaccine, discomfort from the injection, and potential complications brought about by puncturing the skin with the needle. Immunization through the skin without the use of needles (transdermal immunization) represents a major advance for vaccine delivery avoiding the aforementioned drawbacks in needle use.

The transdermal delivery system of the invention is also not concerned with penetration of intact skin by sound or electrical energy. Such a system that uses an electrical field to induce dielectric breakdown of the stratum corneum is disclosed in U.S. Pat. No. 5,464,386.

Moreover, transdermal immunization may be superior to immunization using needles as more immune cells would be targeted by the use of several locations targeting large surface areas of the skin. A therapeutically effective amount of antigen sufficient to induce an immune response may be delivered transdermally either at a single cutaneous location, or over an area of intact skin covering multiple draining lymph node fields (e.g., cervical, axillary, inguinal, epitrochelear, popliteal, those of the abdomen and thorax). Such locations close to numerous different lymphatic nodes at locations all over the body will provide a more widespread stimulus to the immune system than when a small amount of antigen is injected at a single location by intradermal subcutaneous or intramuscular injection. Antigen passing through or into the skin may encounter antigen presenting cells which process the antigen in a way that induces an immune response. Multiple immunization sites may recruit a greater number of antigen presenting cells and the larger population of antigen presenting cells that were recruited would result in greater induction of the immune response. It is conceivable that absorption through the skin into the blood stream will also result in delivery of antigen to the phagocytic cells of the liver, spleen, and bone marrow that are known to serve as the antigen presenting cells. The result would be widespread distribution of antigen to antigen presenting cells to a degree that is rarely, if ever achieved, by current immunization practices.

The transdermal liposome system may be applied directly to the skin and allowed to air dry, held in place with a dressing or patch or absorbent material, applied as an ointment, or otherwise held by a device such as a stocking or shirt or sprayed onto the skin to maximize contact of the liposomes with the skin. The formulation may be applied in an absorbant dressing or gauze. The formulation may be covered with an occlusive dressing such as, for example, plastic film or COMFEEL (Coloplast), or a non-occlusive dressing such as, for example, DUODERM (3M) or OPSITE (Smith & Napheu).

The formulation may be applied to single or multiple sites, to single or multiple limbs, or to large surface areas of the skin by complete immersion. The formulation may be applied directly to the skin. This could include application to large areas of skin including total immersion, or a skin cream.

An immune response may comprise humoral (i.e., antigen-specific antibody) and/or cellular (i.e., antigen-specific lymphocytes such as B cells, CD4$^+$ T cells, CD8$^+$ T cells, CTL, Th1 cells, Th2 cells, and/or T$_{DTH}$ cells) effector arms. Moreover, the immune response may comprise NK cells that mediate antibody-dependent cell-mediated cytotoxicity (ADCC).

The immune response induced by the formulation of the invention may include the elicitation of antigen-specific antibodies and/or cytotoxic lymphocytes (CTL, reviewed in Alving and Wassef, 1994). Antibody can be detected by immunoassay techniques, and the detection of various isotypes (e.g., IgM, IgD, IgA1, IgA2, secretory IgA, IgE, IgG1, IgG2, IgG3, or IgG4) may be expected. An immune response can also be detected by a neutralizing assay.

Antibodies are protective proteins produced by B lymphocytes. They are highly specific, generally targeting one epitope of an antigen. Often, antibodies play a role in protection against disease by specifically reacting with antigens derived from the pathogens causing the disease. Immunization may induce antibodies specific for the immunizing antigen, such as cholera toxin. These antigen-specific antibodies are induced when antigen is delivered through the skin by liposomes.

CTLs are particular protective immune cells produced to protect against infection by a pathogen. They are also highly specific. Immunization may induce CTLs specific for the antigen, such as a synthetic peptide based on a malaria protein, in association with self-major histocompatibility antigen. CTLs induced by immunization with the transdermal delivery system may kill pathogen infected cells. Immunization may also produce a memory response as indicated by boosting responses in antibodies and CTLs, lymphocyte proliferation by culture of lymphocytes stimulated with the antigen, and delayed type hypersensitivity responses to intradermal skin challenge of the antigen alone.

In a viral neutralization assay, serial dilutions of sera are added to host cells which are then observed for infection after challenge with infectious virus. Alternatively, serial dilutions of sera may be incubated with infectious titers of virus prior to inoculation of an animal, and the innoculated animals are then observed for signs of infection.

The transdermal delivery system of the invention may be evaluated using challenge models in either animals or humans, which evaluate the ability of immunization with the antigen to protect the subject from disease. Such protection would demonstrate an antigen-specific immune response. For example, the *Plasmodium faciparum* challenge model may be used as to induce an antigen-specific immune response in humans. Human volunteers may be immunized using the transdermal delivery system containing peptides or proteins derived from the malaria parasite, and then exposed to malaria experimentally or in the natural setting. The *Plasmodium yoelii* mouse malaria challenge model may be used to evaluate protection in the mouse against malaria (Wang et al., 1995).

Alving et al. (1986) injected liposomes comprising lipid A as an adjuvant for inducing an immune response to cholera toxin (CT) in rabbits and to a synthetic protein consisting of a malaria peptide containing four tetra-peptides (Asn-Ala-Asn-Pro) conjugated to BSA. The authors found that the immune response to cholera toxin or to the synthetic malaria protein was markedly enhanced by encapsulating the antigen within the liposomes containing lipid A, compared to similar liposomes lacking lipid A. Several antigens derived either from the circumsporozoite protein (CSP) or from merozoite surface proteins of Plasmodium falcipacrum have been encapsulated in liposomes containing lipid A. All of the malaria antigens that have been encapsulated in liposomes containing lipid A have been shown to induce humoral effectors (i.e., antigen-specific antibodies), and some have been shown to induce cell-mediated responses as well. Generation of an immune response and immunoprotection in an animal vaccinated with a malaria antigen may be assayed by immunofluorescence to whole, fixed malaria sporozoites or CTLs killing of target cells transfected with CSP.

Vaccination has also been used as a treatment for cancer and autoimmune disease. For example, vaccination with a tumor antigen (e.g., prostate specific antigen) may induce an immune response in the form of antibodies, CTLs and lymphocyte proliferation which allows the body's immune system to recognize and kill tumor cells. Tumor antigens useful for vaccination have been described for melanoma (U.S. Pat. Nos. 5,102,663, 5,141,742, and 5,262,177), prostate carcinoma (U.S. Pat. No. 5,538,866), and lymphoma (U.S. Pat. Nos. 4,816,249, 5,068,177, and 5,227,159), all incorporated by reference herein. Vaccination with T-cell receptor peptide may induce an immune response that halts progression of autoimmune disease (Antel et al., 1996; Vandenbark et al., 1996). U.S. Pat. No. 5,552,300, incorporated by reference herein, also describes antigens suitable for treating autoimmune disease.

The following is meant to be illustrative of the present invention; however, the practice of the invention is not limited or restricted in any way by the examples.

EXAMPLE 1

As an example of the present invention applied to transdermal delivery of the antigen cholera toxin, multilamellar liposomes containing dimyristoyl phosphatidylcholine, dimyristoyl phosphatidylglycerol, cholesterol and lipid A (prepared according to Alving et al., 1993; Alving et al., 1995; Richards et al., 1995, incorporated herein by reference) were used to induce an immune response against cholera toxin.

Dimyristoyl phosphatidylcholine (DMPC), dimyristoyl phosphatidylglycerol (DMPG), and cholesterol (Chol) were obtained from Avanti Polar Lipids (Alabaster, Ala.). Lipid A (primarily monophosphoryl) and cholera toxin (CT) were obtained from List Biological Laboratories (Campbell, Calif.). Stock solutions (180 mM DMPC, 20 mM DMPG, and 150 mM Chol) of the lipids in chloroform were stored at −20° C.

Five mls of each stock solution was mixed in a 100 ml pear shaped flask to give a solution of DMPC, DMPG, Chol and lipid A in a mole ratio of 9:1:7.5:0.02, respectively. Using a rotary evaporator, the solvent was removed at 37° C. under negative pressure (approximately 140 torr) for 10 minutes. The lipids were further dried under low vacuum (less than 50 torr) for 1 hour in a dessicator. The liposomes were formed by removing the lipid film from the wall of the flask with 20 ml of swelling solution (sterile water), shaken by hand for 5–10 minutes and briefly vortexed, lyophilized, and stored at −20° C.

These liposomes were mixed in their lyophilized state with cholera toxin (CT) at 5 mg/ml in normal saline (0.154 M NaCl, pH 7.0) to achieve a final concentration of 100 mM with respect to the phospholipids.

BALB/c mice were marked using a stencil (1.6 cm×2.5 cm) to make a 4 cm$^2$ square which was then gently shaved using an electric clipper. This was done without any indication of trauma to the skin of any of the mice. After shaving, the mice were allowed to rest for 24 hours prior to immunization.

A total of 100 μl of the liposome-antigen formulation was applied to 4 cm$^2$ of shaved skin on the back of each BALB/c mouse. Approximately 25 μl of the formulation was applied to the shaved skin, this volume would form a bead on the shaved skin. Using the smooth side of a bent 200 μl pipette tip, the formulation was gently spread to hydrate the patch of shaved skin; the remaining volume was then applied to the patch of shaved skin and adhered to the hydrated skin without difficulty. The formulation was left on each mouse's back for two hours, this amount of time was sufficient for the formulation to turn into a very small layer, but not fully dry or powdery; the mouse did not groom its back during this time. After the one hour immunization, each mouse was gently held by the nape of its neck and the tail, and placed for 15 seconds in a stream of lukewarm tap water flowing over the patch of shaved skin and back towards the tail. The mouse was gently rubbed with gauze and washed a second time.

Boosting immunization was repeated using the same liposome-antigen formulation and technique three weeks after primary immunization.

Anti-cholera toxin antibodies elicited by transdermal immunization with the transdermal delivery system of the invention were measured using an enzyme-linked immunosorbent assay (ELISA) (Glenn et al., 1995, incorporated herein by reference). Solid-phase ELISA was performed in IMMULON-2 polystyrene plates (Dynatech Laboratories, Chantilly, Va.). Wells of the plate were incubated with antigen in PBS overnight (0.1 mg CT per 50 ml) at room temperature, and blocked with 0.5% (w/v) casein for 2 hours at room temperature. Individual mouse sera diluted in a solution of 0.5% (w/v) casein were added and incubated at room temperature. Horseradish peroxidase-conjugated goat anti-mouse IgG (heavy and light) (Bio-Rad Laboratories, Richmond, Calif.) was used as secondary antibody and 2,2'-azino-di(3-ethyl-benzthiazolone) sulphonic acid was used as substrate, reaction was performed for 30 minutes at room temperature. Absorbances were read at 405 nm on a KINETIC MICROPLATE READER (Molecular Devices, San Diego, Calif.) and subtracted for the reactivity of preimmune sera. The linear portion of the dilution series is determined and the result reported is the serum dilution at which the optical density would be equal to 1.

Induction of an immune response to cholera toxin is demonstrated by antigen-specific antibody titers in Table 1. Note that an initial antibody response was achieved after a single immunization and that a boosting response, as denoted by a rise in antibody optical density units, was seen at 4 weeks in all three animals.

TABLE 1

|  | MOUSE #998 | MOUSE #999 | MOUSE #1000 |
| --- | --- | --- | --- |
| WEEK 1 | 233 | 283 | 27 |
| WEEK 4 | 4768 | 5702 | 8045 |

Table 1. Antibody response to cholera toxin. BALB/c mice immunized with cholera toxin in liposomes containing lipid A, applied on the skin. Anti-cholera toxin antibodies measured using ELISA, reported in OD units on individual mice. Mice immunized at 0 and 3 weeks.

EXAMPLE 2

Lyophilized lipids were prepared, and the liposomes were formed in the presence of cholera toxin antigen as in Example 1. The formulation containing cholera toxin was used for transdermal immunization unwashed, or washed by adding approximately 20 volumes of buffer and pelleting the liposomes by centrifugation at 25,000 g to 30,000 g for 20 minutes at 20° C. to 25° C. After removal of the clear (or slightly turbid) supernatant fraction, the liposome pellet was suspended to a final concentration of 500 μg/ml cholera toxin as determined by a modified Lowry assay.

Mice in the unwashed liposome group were immunized transdermally with 100 μl of liposome-antigen formulation (with or without lipid A) as in Example 1; mice in the washed liposome group were immunized transdermally with 500 μl of liposome-antigen formulation (with or without lipid A) as in Example 1. The amount of cholera toxin used in the above cases was 250 μg total antigen.

The saline groups had 100 μl of 2.5 mg/ml (250 μg) cholera toxin applied to the shaved areas for two hours. The oral immunization groups were fed the equivalent of 25 μg of cholera toxin of the liposome-antigen formulation used for transdermal immunization.

As described above, five BALB/c mice were immunized in each group, and then boosted three weeks later.

Induction of an immune response to cholera toxin at week 4 was assayed (Table 2) by measuring antigen-specific antibody using the ELISA method described in Example 1.

TABLE 2

| Immunization Group | Antigen Dose (µg) | Antibody Response |
|---|---|---|
| Unwashed L(LA + CT), transdermal | 250 | 9960 (834–22,476) |
| Unwashed L(CT), transdermal | 250 | 49422 (7180–64306) |
| Washed L(LA + CT), transdermal | 250 | 9 (1–29) |
| Washed L(CT), transdermal | 250 | 5 (0–20) |
| L(LA), transdermal | 250 | 8 (0–42) |
| CT + Saline, transdermal | 250 | 28 (1–359) |
| CT + Saline, oral | 25 | 116 (16–154) |
| Unwashed L(LA + CT), oral | 25 | 53 (16–31) |
| Unwashed L(CT), oral | 25 | 134 (10–335) |

Table 2. Antibody response to cholera toxin. BALB/c mice (n=5) immunized as described in Example 2 at week 0 and week 3 in groups as shown. Anti-cholera toxin IgG antibodies individually measured using ELISA on sera one week after boosting (week 4) and reported as the geometric mean and standard error of the mean of each group. OD units represent the serum dilution at which the optical density is equal to 1. Abbreviations: L is liposome, LA is lipid A, and CT is cholera toxin.

The antigen-specific immune response associated with the groups of unwashed liposome-antigen formulation applied transdermally was measured to demonstrate the kinetics and maintenance of the immune response (Table 3) and the difference in IgG subclasses induced by liposome-antigen formulations with or without lipid A (Table 4).

TABLE 3

| GROUP | WEEK 1 | WEEK 4 | WEEK 6 |
|---|---|---|---|
| L(LA + CT) | 37 (11–27) | 49,422 (7,000–64,000) | 55,572 (36,000–87,000) |
| L(CT) | 28 (11–27) | 9,960 (800–22,000) | 19,533 (11,000–34,000) |

Table 3. Kinetics and maintenance of the antibody response to cholera toxin. BALB/c mice (n=5) immunized as described in Example 2 at week 0 and week 3 in groups as shown and antibody response determined at week 1, 4 and 6. Anti-cholera toxin IgG antibodies individually measured using ELISA and reported as the geometric mean and standard error of the mean for each group. OD units represent the serum dilution at which the optical density is equal to 1. Abbreviations: L is liposome, LA is lipid A, and CT is cholera toxin.

TABLE 4

| Group | IgG1 (µg/ml) | IgG2a (µg/ml) | IgG2b (µg/ml) | IgG3 (µg/ml) |
|---|---|---|---|---|
| L(LA + CT) | 45.3 (25–80) | 7.8 (4–16) | 3.1 (2–4) | 1.9 (1–5) |
| L(CT) | 19.2 (10–35) | 40.2 (20–83) | 8.9 (6–14) | 11.4 (6–22) |

Table 4. IgG subclass antibodies to cholera toxin at week 4. Anti-cholera toxin specific IgG subclass antibodies were measured using a quantitative ELISA as described in Glenn et al. (1995) and reported as the geometric mean and standard error of the mean. Abbreviations: L is liposome, LA is lipid A, and CT is cholera toxin.

EXAMPLE 3

Recombinant dengue-2 envelope protein (DEN-2 E, Smucny et al., 1995) may be used as an antigen in the transdermal delivery system described above. Transdermal application of the liposome-antigen formulation may be used to vaccinate against dengue-2 viral infection and assessed in either animal or human trials.

Three-week old BALE/c mice will be immunized three times with a formulation containing about 1 µg to 250 µg of DEN-2E antigen, either with or without adjuvant using the transdermal delivery system. Boosting immunization will performed at three to four week intervals. Antibodies against DEN-2 E antigen may be measured by ELISA (Smucny et al., 1995) and assayed for cross-reactivity against envelope proteins of serotypes 1, 3 and 4. The mice will be challenged subsequently with an intracerebral injection of 100 times the $LD_{50}$ dose of mouse-adapted dengue-2 virus and observed for for one month for protection against lethal encephalitis.

Pooled sera collected three weeks after the third immunization will be assayed for viral neutralizing activity using a plaque reduction neutralization assay (Russell and Nisalak, 1987). Generally, sera will be serially diluted in two-fold steps from 1:5 to 1:160, and distributed in 24-well plates with 50 p.f.u. of the dengue-2 NGC strain. Suspensions of PS cells (porcine kidney cells as described in Summers and Smith, 1987) (approximately $8 \times 10^4$ cells per well) in L15 medium supplemented with 3% fetal calf serum will be added to each well and the plates will be incubated at 37° C. for 4 hours. An equal volume of 2% carboxymethylcellulose suspension in L15 supplemented with 3% fetal calf serum will then be added to each well. After six days of incubation at 37° C., the PS cells will be rinsed with PBS, fixed with formol solution in PBS, and then permeabilized with 0.5% Triton X-100 in PBS. Focus staining will be performed by successive incubations of cell layers at 37° C. for 1 hour each with HMAF (1:100 in PBS) (hyperimmune ascites fluid to whole dengue virions) followed by peroxidase-labeled goat anti-mouse IgG (BIOSIS, Philadelphia, Pa.). The staining solution (300 µl of 0.05% 3,3'-diaminobenzidine tetrachloride, 0.3% $H_2O_2$, 0.1M Tris-HCl, pH 7.6) will then be added to each well. The reaction will be stopped by adding 200 µl of 1M H2SO4. Stained foci will be observed under a microscope and quantitated. Neutralizing serum titers will be determined as the serum dilution yielding a 50% reduction in plaque number (Delenda et al., 1994). Variations of this technique are described by Smucny et al. (1995) and Fonseca et al. (1994). Other dengue envelope proteins (Delenda et al., 1994; Fonseca et al., 1994) may be used for transdermal immunization and the induction of antigen-specific immune response assessed in a similar fashion.

Multiple dengue envelope proteins from serotypes 1–4 may be used in transdermal immunization: simultaneously, in succession, in the same liposome, in separate liposomes, with or without adjuvants as described previously. Induction of an antigen-specific immune response may be assayed as described above for each serotype, and cross-reactivity between serotypes may or may not occur. A multivalent vaccine against serotypes 1–4 using recombinant dengue envelope proteins from serotypes 1–4 may be achieved though this means.

The disclosures of all patents, as well as all other printed documents, cited in this specification are incorporated herein by reference in their entirety.

While the present invention has been described in connection with what is presently considered to be practical and preferred embodiments, it is understood that the present invention is not to be limited or restricted to the disclosed embodiments but, on the contrary, is intended to cover various modifications and equivalent arrangements included within the spirit and scope of the appended claims.

Thus, it is to be understood that variations in the described invention will be obvious to those skilled in the art without departing from the novel aspects of the present invention and such variations are intended to come within the scope of the claims below.

REFERENCES

Alving, C. R. et al. (1986) Effectiveness of liposomes as potential carriers of vaccines: Applications to cholera toxin and human malaria sporozoite antigen. Vaccine, 4:166–172.

Alving, C. R. (1991) Liposomes as carriers of antigens and adjuvants. J. Immunol. Meth., 140:1–13.

Alving, C. R. (1993) Lipopolysaccharide, lipid A, and liposomes containing lipid A as immunologic adjuvants. Immunobiology, 187:430–436.

Alving, C. R. and Wassef, N. M. (1994) Cytotoxic T lymphocytes induced by liposomal antigens: Mechanisms of immunological presentation. AIDS Res. Hum. Retro., 10(sup. 2):S91–S94.

Alving, C. R. et al. (1993) The preparation and use of liposomes in immunological studies. In: Liposome Technology, vol. 3, (Ed., Gregoriadis, G.), CRC Press, Boca Raton, pp. 317–343.

Alving, C. R. et al. (1995) Liposomes as carriers of peptide antigens: Induction of antibodies and cytotoxic T lymphocytes to conjugated and unconjugated peptides. Immunol. Rev., 145:5–31.

Antel, J. P. et al. (1996) Immunotherapy for multiple sclerosis: From theory to practice. Nature Medicine, 2:1074–1075.

Ausubel, F. M. et al. (1996) Current Protocols in Molecular Biology, Wiley, N.Y.

Banerji, B. and Alving, C. R. (1979) Lipid A from endbtoxin: Antigenic activities of purified fractions in liposomes. J. Immunol., 123:2558–2562.

Bathurst, I. C. et al. (1993) An experimental vaccine cocktail for *Plasmodium falciparum* malaria. Vaccine, 11:449–456.

Blum, H. E. (1995) Variants of hepatitis B, C and D viruses: Molecular biology and clinical significance. Digestion, 56:85–95.

Bodanszky, M. (1993) Peptide Chemistry, Springer-Verlag, New York.

Chang, S. P. et al. (1989) Generalized immunological recognition of the major merozoite surface antigen (gp 195) of *Plasmodium falciparum*. Proc. Natl. Acad. Sci. USA, 86:6343–6347.

Chang, S. P. et al. (1992) A carboxyl-terminal fragment of *Plasmodium falciparum* gp195 expressed by a recombinant baculovirus induces antibodies that completely inhibit parasite growth. J. Immunol., 139:548–555.

Chang, S. P. et al. (1994) Regulation of antibody specificity to *Plasmodium falciparum* merozoite surface protein-1 by adjuvant and MHC haplotype. J. Immunol., 152:3483–3490.

Delenda, C. et al. (1994) Analysis of C-terminally truncated dengue 2 and dengue 3 virus envelope glycoproteins: Processing in insect cells and immunogenic properties in mice. J. Gen. Virol., 75:1569–1578.

Deprez, B. et al. (1996) Comparative efficiencies of simple lipopeptide constructs for in vivo induction of virus-specific CTL. Vaccine, 14:375–382.

Deutscher, M. P. (1990) Guide to Protein Purification, Academic Press, San Diego.

Fonseca, B. A. et al. (1994) Recombinant vaccinia viruses co-expressing dengue-1 glycoproteins prM and E induce neutralizing antibodies in mice. Vaccine, 12:279–285.

Frankenburg, S. et al. (1996) Effective immunization of mice against cutaneous leishmaniasis using an intrinsically adjuvanted synthetic lipopeptide vaccine. Vaccine, 14:923–929.

Fries, L. F. et al. (1992a) Liposomal malaria vaccine in humans: A safe and potent adjuvant strategy. Proc. Natl. Acad. Sci. USA, 89:358–362.

Fries, L. F. et al. (1992b) Safety, immunogenicity, and efficacy of a *Plasmodium falciparum* vaccine comprising a circumsporozoite protein repeat region peptide conjugated to *Pseudomonas aeruginosa* toxin A. Infect. Immun., 60:1834–1839.

Glenn, G. M. et al. (1995) Murine IgG subclass antibodies to antigens incorporated in liposomes containing lipid A. Immunol. Lett., 47:73–78.

Goeddel, D. V. (1990) Gene Expression Technology, Academic Press, San Diego.

Gregoriadis, G. (1993) Liposome Preparation and Related Techniques, 2nd Ed., CRC Press, Boca Raton.

Herrington, D. A. et al. (1991) Safety and immunogenicity of a recombinant sporozoite malaria vaccine against *Plasmodium vivax*. Am. J. Trop. Med. Hyg., 45:695–701.

Jahrling, P. B. et al. (1996) Passive immunization of Ebola virus-infected cynomolgus monkeys with immunoglobulin from hyperimmune horses. Arch. Virol. Suppl., 11:135–140.

Janson, J.-C. and Ryden, L. (1989) Protein Purification, VCH, New York.

Katkov, W. N. (1996) Hepatitis vaccines. Med. Clin. North Am., 80:189–200.

Khusmith, S. et al. (1991) Protection against malaria by vaccination with sporozoite surface protein 2 plus CS protein. Science, 252:715–718.

Kriegler, M. (1990) Gene Transfer and Expression, Stockton Press, New York.

Lieberman, J. M. and Greenberg, D. P. (1996) Hepatitis A and B vaccines in children. Adv. Pediatr. Infect. Dis., 11:333–363.

Malik, A. et al. (1991) Human cytotoxic T lymphocytes against the *Plasmodium falciparum* circumsporozoite protein. Proc. Natl. Acad. Sci. USA, 88:3300–3304.

Mast, E. E. and Krawczynski, K. (1996) Hepatitis E: An overview. Annu. Rev. Med., 47:257–266.

Migliorini, P. et al. (1993) Malaria vaccine: Immunization of mice with a synthetic T cell helper epitope alone leads to protective immunity. Eur. J. Immunol., 23:582–585.

Nohria, A. and Rubin, R. H. (1994) Cytokines as potential vaccine adjuvants. Biotherapy, 7:261–269.

Paul, A. and Cevc, G. (1995) Noninvasive administration of protein antigens: Transdermal immunization with bovine serum albumin in transfersomes. Vaccine Res., 3:145–164.

Paul, A. et al. (1995) Transdermal immunization with large proteins by means of ultradeformable drug carriers. Eur. J. Immunol., 25:3521–3524, 1995.

Pessi, A. et al. (1991) Lack of H-2 restriction of the *Plasmodium falciparum* (NANP) sequence as multiple antigen peptide, Eur. J. Immunol., 24:2273–2276.

Plotkin, S. A. and Mortimer Jr., E. A. (1994) Vaccines, 2nd Ed., W. B. Saunders, Philadelphia.

Richards, R. L. et al. (1988) Liposomes, lipid A, and aluminum hydroxide enhance the immune response to a synthetic malaria sporozoite antigen. Infect. Immun., 56:682–686.

Richards, R. L. et al. (1995) A compendium of vaccine adjuvants and excipients. In: Vaccine Design (Eds., Powell, M. F. and Newman, M. J.), Plenum, New York.

Russell, P. K. and Nisalak, A. (1987) Dengue virus identification by the plaque reduction neutralization test. J. Immunol., 99:291–296.

Scopes, R. K. (1993) Protein Purification, Springer-Verlag, New York.

Shafara, A. et al. (1995) Hepatitis C. Ann. Intern. Med., 125:658–668.

Skeiky, Y. A. W. et al. (1995) A recombinant Leishmania antigen that stimulates human peripheral blood mononuclear cells to express a Th1-type cytokine profile and to produce interleukin 12. J. Exp. Med., 181:1527–1537.

Smedile, A. et al. (1994) Advances in hepatitis D virus biology and disease. Prog. Liver Dis., 12:157–175.

Smucny, J. J. et al. (1995) Murine immunoglobulin G subclass responses following immunization with live dengue virus or a recombinant dengue envelope protein. Am. J. Trop. Med. Hyg., 53:432–437.

Summers, M. D. and Smith, G. E. (1987) A manual of methods for baculovirus vectors and insect cell culture procedure. Texas Agricultural Experiment Station Bulleting, No. 1555.

Tam, J. P. (1988) Synthetic peptide vaccine design: Synthesis and properties of a high-density multiple antigenic peptide system. Proc. Natl. Acad. Sci. USA, 85:5409–5413.

Vandenbark, A. A. et al. (1996) Treatment of multiple sclerosis with T-cell receptor peptides: Results of a double-blind pilot trial. Nature Medicine, 2:1109–1115.

Vreden, S. G. S. et al. (1991) Phase I clinical trial of a recombinant malaria vaccine consisting of the circumsporozoite repeat region of *Plasmodium falciparum* coupled to hepatitis B surface antigen, Am. J. Trop. Med. Hyg., 45:533–538.

Wang, R. et al. (1995) Induction of protective polyclonal antibodies by immunization with a *Plasmodium yoelii* circumsporozoite protein multiple antigen peptide vaccine. J. Immunol., 154:2784–2793.

Wertz, P. W. (1992) Liposome dramatics: Chemicals aspects of the skin lipid approach. In: Liposome Dramatics (Eds., Braun-Falco, O. et al.), Springer-Verlag, New York, pp. 38–43.

White, K. et al. (1993) Induction of cytolytic and antibody responses using *Plasmodium falciparum* repeatless circumsporozoite protein encapsulated in liposomes. Vaccine, 11:1341–1346.

Wiesmueller, K.-H. et al. (1991) The antibody response in BALB/c mice to the *Plasmodium falciparum* circumsporozoite repetitive epitope covalently coupled to synthetic lipopeptide adjuvant. Immunology, 72:109–113.

Wisdom, G. B. (1994) Peptide Antigens, IRL Press, Oxford.

What we claim is:

1. A method of inducing an immune response to an antigen comprising:

(a) applying a formulation to intact skin of an organism, wherein the formulation comprises liposomes and the antigen; and (b) inducing the immune response in the organism without perforating the skin, wherein the immune response is specific for the antigen.

2. The method of claim 1, wherein the immune response comprises an antigen-specific lymphocyte.

3. The method of claim 2, wherein the immune response comprises activation of an antigen-specific B cell.

4. The method of claim 3, wherein the immune response further comprises an antigen-specific antibody.

5. The method of claim 4, wherein the immune response further comprises antibody-dependent cell-mediated cytotoxicity.

6. The method of claim 2, wherein the immune response comprises activation of an antigen-specific cytotoxic T cell.

7. The method of claim 2, wherein the immune response comprises activation of an antigen-specific helper T cell.

8. The method of claim 2, wherein the immune response comprises activation of an antigen-specific delayed-type hypersensitivity T cell.

9. The method of claim 1, wherein induction of the immune response is detected by lymphoproliferation or a viral neutralization assay.

10. The method of claim 1, wherein the antigen has a molecular weight greater than 800 daltons.

11. The method of claim 1, wherein the antigen is derived from a pathogen, a tumor cell, or a normal cell.

12. The method of claim 1, wherein the antigen is derived from a pathogen selected from the group consisting of bacterium, virus, fungus, Rickettsia, and parasite.

13. The method of claim 1, wherein the antigen is a tumor antigen.

14. The method of claim 1, wherein the antigen is an autoantigen.

15. The method of claim 1, wherein the antigen is selected from the group consisting of carbohydrate, glycolipid, glycoprotein, lipid, lipoprotein, peptide, phospholipid, and protein.

16. The method of claim 15, wherein the antigen is obtained by recombinant means or purification.

17. The method of claim 15, wherein the antigen is obtained by chemical synthesis.

18. The method of claim 1, wherein the antigen is a peptide or a protein of greater than 800 daltons molecular weight.

19. The method of claim 1, wherein the liposomes are unilamellar.

20. The method of claim 1, wherein the liposomes are paucilamellar, or multilamellar.

21. The method of claim 1, wherein the liposomes are formed from phospholipid, or a mixture of phospholipid and sterol.

22. The method of claim 21, wherein the phospholipid is selected from the group consisting of phosphatidylcholine, phosphatidylglycerol, diphosphatidylglycerol, phosphatidylserine, phosphatidic acid, phosphatidylinositol, lysophosphatide, sphingomyelin, and mixtures thereof.

23. The method of claim 21, wherein the sterol comprises cholesterol.

24. The method of claim 1, wherein the liposomes are formed from a nonionic amphiphile.

25. The method of claim 24, wherein the nonionic amphiphile is selected from the group consisting of polyoxyethylene fatty acid ester, polyoxyethylene fatty acid ether, diethanolamide, long chain acyl hexosamide, long chain acyl amino acid amide, long chain amino acid amine, polyoxyethylene sorbitan ester, polyoxyethylene glyceryl ester, polyoxyethylene glyceryl diester, glycerol stearate, glycerol distearate, glycerol oleate, glycerol dioleate, glycerol palmitate, glycerol dipalmitate, and mixtures thereof.

26. The method of claim 1, wherein the liposomes are formed from an ionic amphiphile.

27. The method of claim 26, wherein the ionic amphiphile is selected from the group consisting of betaine, sarcosinate, monomeric alkyd, dimeric alkyd, dimethyl distearyl amine, and mixtures thereof.

28. The method of claim 1, wherein the formulation further contains an adjuvant.

29. The method of claim 1, wherein the formulation is applied to intact skin overlying more than one draining lymph node field.

* * * * *